United States Patent [19]

Mahood

[11] Patent Number: 5,605,947

[45] Date of Patent: Feb. 25, 1997

[54] AMORPHOUS NEO-DIOL PHOSPHITE COMPOSITIONS

[75] Inventor: James A. Mahood, Morgantown, W. Va.

[73] Assignee: General Electric Company, Pittsfield, Mass.

[21] Appl. No.: 361,263

[22] Filed: Dec. 21, 1994

Related U.S. Application Data

[63] Continuation-in-part of Ser. No. 307,545, Sep. 16, 1994, Pat. No. 5,424,348, which is a continuation of Ser. No. 96,530, Jul. 22, 1993, abandoned.

[51] Int. Cl.$^6$ .............................. C08K 5/17; C08K 5/527; C07F 9/6574
[52] U.S. Cl. ............................ 524/117; 524/251; 524/252
[58] Field of Search .......................... 558/85, 71; 524/117

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,560,434 | 2/1971 | Abramoff . |
| 3,644,280 | 2/1972 | Tazewell . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 3,886,114 | 5/1975 | Beadle . |
| 3,969,315 | 7/1976 | Beadle . |
| 4,086,304 | 4/1978 | Hutton et al. . |
| 4,116,926 | 9/1978 | York . |
| 4,196,117 | 4/1980 | Spivack . |
| 4,318,845 | 3/1982 | Spivack et al. . |
| 4,405,739 | 9/1983 | Kinson . |
| 4,529,533 | 7/1985 | Chasar . |
| 4,650,894 | 3/1987 | Fisch et al. . |
| 4,666,959 | 5/1987 | Weissberger et al. . |
| 4,673,701 | 6/1987 | Minagawa et al. . |
| 4,707,509 | 11/1987 | Fisch et al. . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,925,888 | 5/1990 | Aumueller et al. . |
| 4,956,406 | 9/1990 | Myers et al. . |
| 4,957,954 | 9/1990 | Iizuka et al. . |
| 4,957,956 | 9/1990 | Neri et al. . |
| 5,039,723 | 8/1991 | Haruna et al. . |

FOREIGN PATENT DOCUMENTS

| | | |
|---|---|---|
| 0392392 | 10/1990 | European Pat. Off. . |
| 0400454 | 12/1990 | European Pat. Off. . |
| 0576833 | 1/1994 | European Pat. Off. . |
| 0635514 | 1/1995 | European Pat. Off. . |
| 0635514A1 | 1/1995 | European Pat. Off. . |
| 2944254 | 5/1980 | Germany . |
| 2087399 | 5/1982 | United Kingdom . |

Primary Examiner—Veronica P. Hoke

[57] ABSTRACT

A phosphite is provided having the formula:

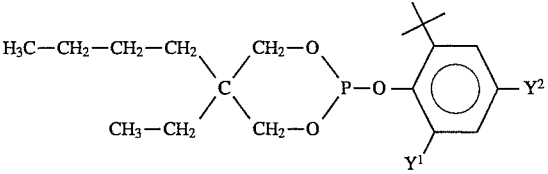

wherein $Y^1$ is an alkyl group and $Y^2$ is selected from the group consisting of sec-butyl and tert-butyl. A solid amorphous phosphite composition is also provided which preferably contains an aliphatic polyamine. The phosphite exhibits enhanced stability including hydrolyric and UV stability, and is useful in stabilizing thermoplastic compositions. The phosphite composition exhibits further enhancements in hydrolytic stability, and is useful in stabilizing thermoplastic compositions.

17 Claims, No Drawings

AMORPHOUS NEO-DIOL PHOSPHITE COMPOSITIONS

This continuation-in-part of application Ser. No. 08/307,545 filed on Sep. 16, 1994, now U.S. Pat. No. 5,424,348, which is a continuation of Ser. No. 096,530, filed Jul. 22, 1993, abandoned.

BACKGROUND OF THE INVENTION

1. Field of the Invention

The present invention relates to phosphites, and more particularly related to neoalkyl phenyl phosphites and amorphous neo-alkyl phenyl phosphite compositions.

2. Description of the Related Art

Neoalkyl phenyl phosphites are known, see Dever et al U.S. Pat. No. 3,714,302 which is incorporated herein by reference. Dever et al teaches neoalkyl phenyl phosphites of the formula:

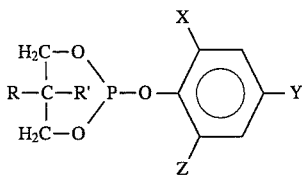

wherein R and R' are independently lower alkyl groups and X, Y and Z are independently selected from the group consisting of —H and alkyl groups of from 1 to 5 carbon atoms, providing that the sum of the carbon atoms in X, Y and Z does not exceed 5, may be simply and economically produced by the reaction of a neoglycol with $PCl_3$ in the absence of a catalyst, HCl acceptor and solvent to produce a crude product of the formula:

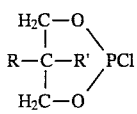

wherein R and R' are defined above, followed by reaction with phenol or a compound of the formula:

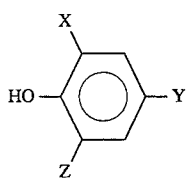

in which X, Y and Z are defined above. The desired product of Dever et al. may be recovered by distillation.

Suitable glycols are listed and include 2-ethyl-2-butyl-1,3 propane diol among others.

Dever et al. U.S. Pat. No. 3,714,302 clearly teaches away from compounds wherein X and Z are both alkyl groups such that they create stearic hinderance. Specifically note col. 3, lines 63 to 65 thereof wherein it states that the proviso that the sum of X, Y and Z does not exceed 5 excludes such phenols as 2,6-di-tertiarybutyl phenols from consideration because of stearic hinderance problems.

Dever et al U.S. Pat. No. 3,467,733 discloses compounds of the formula:

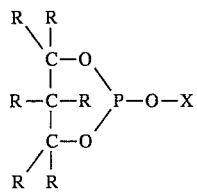

wherein R is independently selected from the Group consisting of hydrogen, alkyl of 1 to 6 carbon atoms, and halogen; X is a monovalent radical of the formula:

wherein $R^2$ independently selected from the Group consisting of hydrogen, alkyl of 1 to 12 carbon atoms and halogen, and $R^3$ is independently selected from the group consisting of alkyl of 1 to 12 carbon atoms and halogen, and sets forth in Claim 7 a phosphite of the formula:

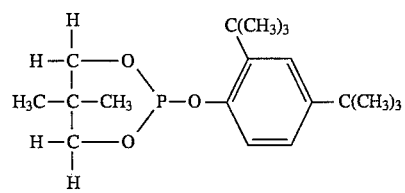

Many of these phosphites can, however, experience thermal stability problems, hydrolyric stability problems, and/or ultraviolet light discoloration problems. Ultraviolet light stabilizers and amines such as trisopropanolamine have been utilized in conjunction with various types of phosphites to enhance the hydrolyric stability thereof, but there still remains a need to enhance the various properties of phosphite compositions.

Consequently, there is a need for a neoalkyl aryl phosphite and neoalkyl phenyl phosphite compositions exhibiting improved ultraviolet and hydrolyric stability.

SUMMARY OF THE INVENTION

The present invention involves a neoalkyl aryl phosphite of the formula:

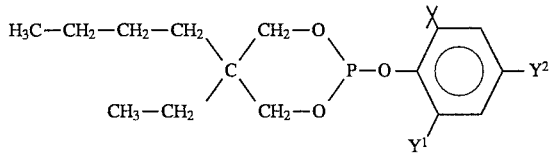

wherein $Y^1$ is independently selected from the group consisting of alkyl radicals, and preferably $Y^1$ is a tert-butyl group and $Y^2$ is a tert-butyl. The phosphites are useful to stabilize organic materials against thermal oxidative degradation, exhibit enhanced hydrolyric stability and are resistant to UV yellowing. The present invention further involves an amorphous phosphite composition containing the above neo-alkyl aryl phosphite. The amorphous phosphite composition exhibits greatly enhanced hydrolyric stability.

DETAILED DESCRIPTION OF THE INVENTION

The amorphous phosphite composition utilizes the above phosphite in solid amorphous form, and preferably contains respective amounts of (a) a neo-alkyl aryl phosphite and (b) an amine preferably an aliphatic polyamine. The amorphous phosphite composition is formed by preparing a melt mixture of the phosphite and polyamine to form a melt composition and then rapidly cooling the melt composition to form a solid amorphous phosphite composition. The amorphous nature of the composition appears to greatly enhance the hydrolyric stability of the solid composition compared to crystalline composition containing the same constituents. The phosphite is a compound of the formula:

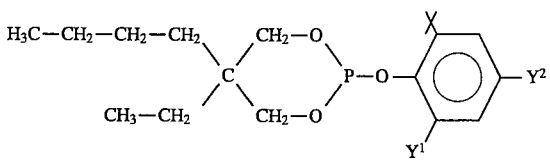

The phosphite may be made by the reaction of 2-ethyl-2-butyl-1,3-propane diol with $PCl_3$ in the absence of a catalyst, HCl acceptor and solvent to produce an intermediate product of the formula:

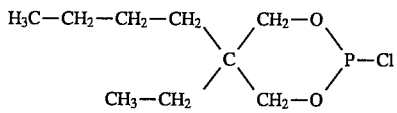

followed by the reaction with a hydroxyaryl compound of the formula:

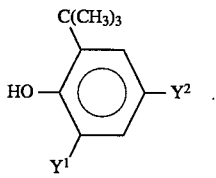

wherein $Y^1$ and $Y^2$ are as defined above. Suitable reaction methods are set out in Great Britain Patent 2087399A, Spivak et al. U.S. Pat. No. 4,318,845 issued 1982, and Article in Phosphourous & Sulfur Journal by J. D. Spivak et al. 1983, vol. 15, pp. 9–13, all of which are incorporated herein by reference.

The reaction between the diol and $PCl_3$ may be conducted in known manner, as by mixing the reactants together at room temperature, or preferably, by cooling the $PCl_3$ to a temperature between 5–50 degrees centigrade prior to addition of diol to the reactor. An excess of either reactant may be employed although it is preferred to operate with substantially stoichiometric amounts of the diol and $PCl_3$. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

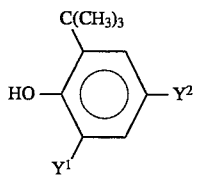

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stoichiometric amount of amine acceptor should be present. $Y^2$ is a t-butyl group. When $Y^2$ is a t-butyl group the phosphite is a solid at room temperature (25° C.).

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-t-butyl-6-alkyl phenyl group because such groups have corresponding 2,4-di-t-butyl-6-alkyl phenol degradation products which have a boiling point of greater than 260° C.

The amines are preferably polyamines, and more preferably aliphatic polyamines. The aliphatic polyamine preferably has a boiling point of greater than 175°, more preferably greater than 190°, and most preferably greater than 200° C. The aliphatic polyamine may contain primary, secondary or tertiary amine groups. Preferably the amine groups are primary amine groups. The polyamine may contain 2, 3 or more amine groups, and in other words may be a diamine, triamine or greater polyamine amine. The preferred polyamines are aliphatic primary diamines of the formulas

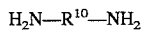

wherein $R^{10}$ is selected from $C_6$ to $C_{10}$ divalent alkyl radicals, and more preferably the diamine is selected from 1,6 diaminohexane and 1,10-diaminodecane. Suitable aliphatic secondary diamines may be represented by the general formula:

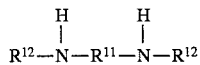

wherein $R^{11}$ is selected from $C_1$ to $C_{10}$ divalent alkyl radicals and $R^{12}$ is selected from $C_1$ to $C_{30}$ monovalent alkyl radical. Suitable aliphatic tertiary diamines may be represented by the general formula

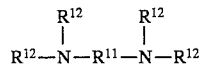

wherein $R^{11}$ and $R^{12}$ are defined as above. Most preferably the polyamine is an aliphatic primary diamine. The amines may also be monoamines and hydroxylamines such as triisopropanolamine, and $R^{12}HH_2$, $R^{12}{}_2NH$, $R^{12}{}_2NOH$.

The present invention also involves a process involving the melt blending of a crystalline phosphite and an amine to form a melt blend, and cooling the melt blend to form an amorphous solid phosphite composition. The process may also involve storing the phosphite for a period in excess of 10 days (possibly in humid conditions (>60% relative humidity)) at ambient temperature, and then compounding the phosphite composition with a thermoplastic polymer such as a polyolefin, for example polypropylene for thermal oxidative stability thereof.

The amorphous stabilizer composition of the present invention preferably comprises at least 50 percent by weight of the phosphite based on the total weight of the stabilizer composition, more preferably comprises from 80 percent by weight to 99.9 percent by weight of the phosphite based on the total weight of the stabilizer composition, more preferably from 90 to 99.8 percent by weight thereof, more preferably from 95 to 99.5 percent by weight thereof, and most preferably from 97 to 99 percent by weight thereof. The amine is preferably present at a level of from 0.1 to 10 percent by weight based on the total weight of the stabilizer composition, more preferably from 0.2 to 10 percent by weight thereof, more preferably present at a level of from 0.6 to 5 percent by weight thereof, and most preferably from 1 to 3 percent by weight thereof. The stabilizer composition is in the form of amorphous (noncrystalline) particles, such as powders and pellets. The stabilizer composition preferably contains less than 10 percent by weight of other materials such as polymeric materials and other organic materials such as waxes, synthetic and petroleum dried lubricating oils and greases; animal oils such as for example fat, tallow, lard, cod liver oil, sperm oil; vegetable oil such as caster, linseed, peanut, cod seed, and the like; fuel oil, diesel oil, gasoline, and the like. In other words, the stabilizer composition, is preferably substantially free of other materials, in other words, containing less than 1 percent of other organic materials, and more preferably is free of other organic materials. Optionally, the stabilizer composition is essentially free of monoamines, such as triisopropylamine. The compositions of the present invention are preferably amorphous to ensure homogeneity of the compositions. The present compositions are preferably obtained by melt mixing rather than simple mechanical blending or solution blending, and surprisingly and unexpectedly the compositions made by melt mixing show superior hydrolyric stability over similar compositions made by simple mechanical (dry) or solution blending.

The present invention also is a stabilized polymer composition which includes an effective amount of the phosphite described above. An amount of the phosphite of the invention is considered to be an "effective amount" when the polymer composition containing the phosphite of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxie, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)propane) terephthalate and polyhydroxybenzoates as well as blockcopolyetheresters derived from polyethers having hydroxyl end groups.

Polyamides and copolyamides which are derived from diamines and dicarboxylic acids and/or from aminocarboxylic acids or the corresponding lactams, such as polyamide, 4,polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6-di-tertbutyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)- 4,6 dimethylphenol, 2,6-di-octadecyl-4-methylphenol, 2,4,6,-tricyclohexyphenol, 2,6-di-tert-butyl-4methoxymethylphenol.

1.2 Alkylated hydroquinones, for example, 2,6-di-tertbutyl-4-methoxyphenol, 2,5-di-tert-butyl-hydroquinone, 2,5-di-tert-amylhydroquinone, 2,6-diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl(phenol), 2,2'-methylene-bis-(4-methyl-6-cyclohexylphenol), 2,2'-methylene-bis(6-nonyl-4-methylphenol), 2,2'-methylene-bis-(6- nonyl-4-methylphenol), 2,2'-methylene-bis-(6-(alphamethylbenzyl)-4-nonylphenol), 2,2'-methylene-bis-(6-(alpha,alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy- 5-methylphenyl)-dicyclopentadiene, di-(2-(3'-tert-butyl-2'hydroxy-5'methylbenzyl)-6-tert-butyl-4-methylphenyl)terephthalate.

1.5 Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5-dicyclohexyl-4-hydroxybenzyl) isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)-carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)hexamethylenediamine, N,N'-di-(3,5-di-tert-butyl-4-hydroxyphenylpropionyl)trimethylenediamine, N,N'-di-(3,5-di-tert-butyl-4-hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl-5'-tert-butyl-,5'(1,1,3,3-tetramethylbutyl)-,5-chloro-3',5'-di-tert-butyl-,5-chloro-3'tert-butyl-5'methyl-,3'sec-butyl-5'tert-butyl-,4'-octoxy,3',5'-ditert-amyl-3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4-dodecyloxy-,4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxycinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam.

2.7 Oxalic acid diamides, for examples, 4,4'-dioctyloxy-oxanilide, 2,2'-di-octyloxy-5',5'-di-tert-butyloxanilide, 2,2'-di-dodecyloxy-5',5'-di-tert-butyl-oxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzylidenoxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate; ethyl-3-(N,N-dibenzylaminoxy)propanonoate; 1,6-hexamethylenebis-(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils, such as epoxidized soybean oils, lubricants, emulsifiers, pigments, hydroxylamines such as $R_2NOH$ wherein R is a $C_1$ to $C_{30}$ alkyl group, such as propyl or stearyl, optical brighteners, flameproofing agents, anti-static agents, blowing agents and thiosynergists such as dilaurythiodipropionate or distearylthiodipropionate.

Polymeric particles may be coated with the present stabilizer compositions alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by support Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti and Zr.

Consistent with the invention, the amorphous stabilizer compositions of the invention may be added to the polymer at any time prior to or during fabrication into articles and may be combined with the polymer by any of a variety of means known in the art, such as by preblending or by being fed directly into fabrication equipment.

The following examples illustrate the present invention.

EXAMPLES

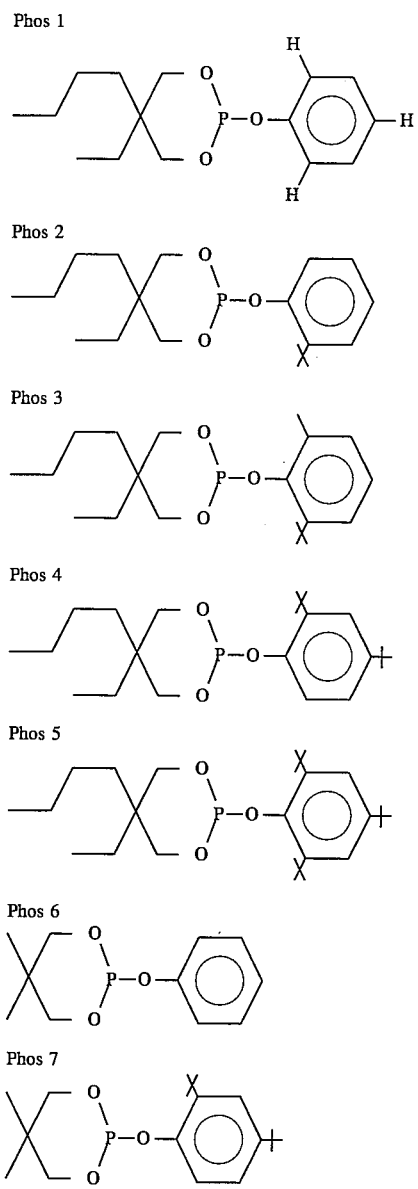

The Examples set out the half-life of phosphites in films pressed from a polypropylene resin composition containing 1% by weight of the respective phosphite. Half-life was measured at the time to ½ depletion of the initial phosphite loading upon exposure of the film to a temperature of 60° C. and a nominal relative humidity of 75%. It is believed that degradation of the phosphite in the film was due primarily to hydrolysis of the phosphite. Phos 5 illustrates the phosphites of the present invention and their results are shown in example 1. Examples A, B, C, D, E & F are comparative examples. The additive is compounded into polymer at 5000–10000 ppm, and the initial color recorded. The polymer sample is then exposed to short wave UV light (as the 254 mm light from a Mineralite® Lamp. Model UVGL-5) for a set time interval (usually 10 min.) at a set distance from the light source (usually less than 1 inch). The color of the polymer sample is recorded and the change in yellowness index (delta YI) is calculated. Samples that fail the UV yellowing test will have a delta YI>5, typically in the 20–40 range. Samples that pass the UV yellowing test will have delta YI<5, typically in the 0–2 range.

TABLE I

| Example | Phos Type | t ½ (days) | U.V. Yellowing |
|---|---|---|---|
| A | Phos 1 | 4 | No |
| B | Phos 2 | 15 | Yes |
| C | Phos 3 | 21 | No |
| D | Phos 4 | 22 | Yes |
| 1 | Phos 5 | 37 | No |
| E | Phos 6 | <2 | No |
| F | Phos 7 | 12 | Yes |

Note the greater hydrolyric stability of the phosphites of the present invention over the comparative phosphites. Also note the resistance of Example 1 to U.V. yellowing. Table II illustrates the high boiling point of the degradation phenolic of Example 1. The data herein demonstrates the improved properties and combination of properties of the phosphites of the present invention. The diol of the phosphite of the present invention provides enhanced hydrolytic stability over the lower molecular weight diols of Phos 6 and Phos 7 (compare Phos 5 with Phos 7).

The above examples show the superior performance and properties of Phos 5 over the comparative phosphites.

TABLE II

| Phenolic | Boiling Point |
|---|---|
| HO—⟨phenol with X substituent⟩ | 230° C. |
| HO—⟨phenol with X and t-butyl⟩ | 235° C. |
| HO—⟨phenol with X⟩ | 237° C. |
| HO—⟨phenol with X and t-butyl⟩ | 263° C. |
| HO—⟨phenol with X and t-butyl⟩ | 269° C. |
| HO—⟨phenol with X and t-butyl⟩ | 278° C. |

The examples below show the superior performance of amorphous solid phosphite compositions over comparative compositions.

Example G was a crystalline state of Phos 5. Example 3 was Phos 5 is a glass amorphous state. Example 5 was an amorphous melt blend of 99 wt % Phos 5 and 1 wt % Tinuvin 770 Bis(2,2,6,6,-tetramethylpiperidyl)sebacate. Example 4 was an amorphous melt blend containing 99 wt % Phos 5 and 1 wt % trioctyl amine. Example 2 was an amorphous melt blend (solid form) containing 99 wt % Phos 5 and 1 wt % 1,10-diaminodecane. Note the superior performance of Example 2 over Examples 5 and 4. Note the superior performance of Example 3 over Example G and further note the superior performance of Examples 5 and 4 over Example G. The samples were exposed to 75% nominal relative humidity at room temperature (approx. 70° F.) for extended periods of time, and these various levels of hydrolyric stability are evidenced by percent weight gain with the lower percentages of weight gain at a given level of exposure time evidencing higher levels of hydrolyric stability.

TABLE III

Samples Aged at room temperature under nominal 75% relative humidity

| Hours | Ex 5 | Ex 4 | Ex 2 | Ex 3 | Ex G |
|---|---|---|---|---|---|
| 0 | 0.00 | 0.00 | 0.00 | 0.00 | 0.00 |
| 72 | 0.10 | 0.05 | 0.07 | 0.04 | 0.03 |
| 144 | 0.14 | 0.13 | 0.14 | 0.10 | 0.29 |
| 168 | 0.12 | 0.19 | 0.10 | 0.12 | 0.62 |
| 240 | 0.11 | 0.10 | 0.12 | 0.29 | 2.30 |
| 312 | 0.13 | 0.12 | 0.13 | 0.59 | #N/A |
| 456 | 0.13 | 0.09 | 0.12 | 1.82 | #N/A |
| 504 | 0.14 | 0.09 | 0.16 | 2.39 | #N/A |
| 576 | 0.13 | 0.08 | 0.14 | #N/A | #N/A |
| 840 | 0.16 | 0.14 | 0.20 | #N/A | #N/A |
| 936 | 0.18 | 0.20 | 0.13 | #N/A | #N/A |
| 1080 | 0.40 | 0.56 | 0.14 | #N/A | #N/A |
| 1248 | 1.26 | 1.94 | 0.18 | #N/A | #N/A |
| 1416 | #N/A | #N/A | 0.18 | #N/A | #N/A |
| 1584 | #N/A | #N/A | 0.21 | #N/A | #N/A |
| 1776 | #N/A | #N/A | 0.24 | #N/A | #N/A |
| 2112 | #N/A | #N/A | 0.26 | #N/A | #N/A |
| 2280 | #N/A | #N/A | 0.20 | #N/A | #N/A |
| 2496 | #N/A | #N/A | 0.26 | #N/A | #N/A |
| 2952 | #N/A | #N/A | 0.21 | #N/A | #N/A |
| 3312 | #N/A | #N/A | 0.28 | #N/A | #N/A |
| 3528 | #N/A | #N/A | 0.22 | #N/A | #N/A |
| 3936 | #N/A | #N/A | 0.26 | #N/A | #N/A |
| 4608 | #N/A | #N/A | 0.4 | #N/A | #N/A |

The amorphous form of the phosphite clearly yielded substantial improvements in hydrolytic stability over the crystalline form. The amorphous composition utilizing the aliphatic diamine exhibited substantially superior results over compositions containing monoamines. Amorphous means that the material has no apparent crystalline form, and can be readily determined by conventional x-ray powder diffraction exhibiting no detectable refraction.

I claim:

1. An amorphous phosphite composition, comprising phosphite of the formula:

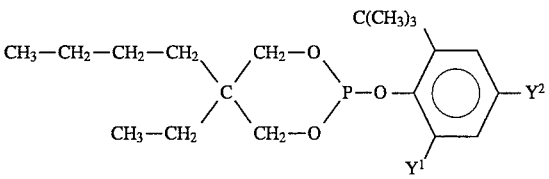

wherein $Y^1$ is alkyl and $Y^2$ is t-butyl and said phosphite is in solid amorphous form.

2. The phosphite composition of claim 1 wherein $Y^1$ is methyl.

3. An amorphous solid phosphite composition, comprising: a phosphite of the formula:

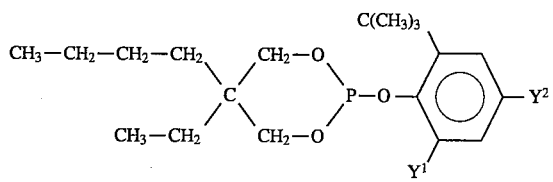

wherein $Y^1$ is alkyl and $Y^2$ is t-butyl and said phosphite is in solid amorphous form, and an amine.

4. A thermoplastic polymeric composition comprising a thermoplastic resin and from 0.01 to 1.0 percent by weight of a phosphite composition as claimed in claim 1 based on the total weight of the composition.

5. A thermoplastic polymeric composition comprising a thermoplastic resin and from 0.01 to 1.0 percent by weight of a phosphite composition as claimed in claim 2 based on the total weight of the composition.

6. A thermoplastic polymeric composition comprising a thermoplastic resin and from 0.01 to 1.0 percent by weight of a phosphite composition as claimed in claim 3 based on the total weight of the composition.

7. A thermoplastic composition as claimed in claim 4 wherein said thermoplastic resin is selected from the group consisting of polyolefins, polycarbonates, polyesters, polyvinyl chloride and polystyrenes.

8. A thermoplastic composition as claimed in claim 4 wherein said thermoplastic resin is polypropylene.

9. A thermoplastic composition as claimed in claim 4 wherein said composition consists essentially of said thermoplastic resin and said phosphite composition.

10. A thermoplastic composition as claimed in claim 9 wherein said $Y^1$ is a tert-butyl group.

11. An amorphous solid phosphite composition, comprising: a phosphite of the formula:

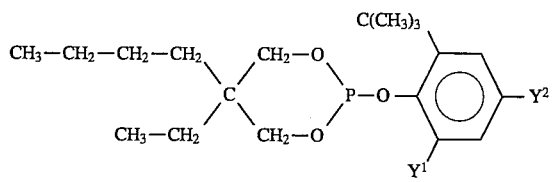

wherein $Y^1$ is alkyl and $Y^2$ is t-butyl and said phosphite is in solid amorphous form, and an aliphatic polyamine.

12. The amorphous composition of claim 1 wherein said phosphite is present at a level of at least 50 percent by weight based on the total weight of the composition.

13. The amorphous composition of claim 11 wherein $Y^1$ and $Y^2$ are each tert-butyl groups.

14. The amorphous composition of claim 11 consisting essentially of said phosphite and said aliphatic polyamine.

15. The amorphous composition of claim 1 comprising from 80 to 99.9 percent by weight of the phosphite based on the total weight of composition.

16. The amorphous composition of claim 1 comprising from 90 to 99.8 percent by weight of the phosphite based on the total weight of composition.

17. The amorphous composition of claim 1 comprising from 95 to 99.5 percent by weight of the phosphite based on the total weight of composition.

\* \* \* \* \*